(12) United States Patent
Reaux (10) Patent No.: US 7,540,039 B2
(45) Date of Patent: Jun. 2, 2009

(54) FACE AND EYE COVERING DEVICE

(76) Inventor: Brian K. Reaux, 710 Rock Hill Dr., Red Oak, TX (US) 75154

( * ) Notice: Subject to any disclaimer, the term of this patent is extended or adjusted under 35 U.S.C. 154(b) by 379 days.

(21) Appl. No.: 10/872,034

(22) Filed: Jun. 18, 2004

(65) Prior Publication Data

US 2005/0015860 A1 Jan. 27, 2005

Related U.S. Application Data (60) Provisional application No. 60/479,652, filed on Jun. 19, 2003.

(51) Int. Cl.
*A42B 1/08* (2006.01)
(52) U.S. Cl. .............................. 2/424; 2/9; 2/15; 2/173; 2/206; 2/432; 2/434; 2/438; 128/201.15
(58) Field of Classification Search ............... 2/424, 2/9, 15, 11, 432, 434, 173, 206, 438; 128/857, 128/201.17, 201.24, 206.19, 201.14, 201.15
See application file for complete search history.

(56) References Cited

U.S. PATENT DOCUMENTS

| | | | |
|---|---|---|---|
| 4,037,593 A | 7/1977 | Tate, Jr. | |
| 4,076,373 A * | 2/1978 | Moretti | 359/507 |
| 4,384,577 A * | 5/1983 | Huber et al. | 128/206.19 |
| 4,419,993 A | 12/1983 | Petersen | |
| 4,428,081 A | 1/1984 | Smith | |
| 4,454,881 A * | 6/1984 | Huber et al. | 128/206.15 |
| 4,600,002 A * | 7/1986 | Maryyanek et al. | 128/206.19 |
| 4,716,601 A | 1/1988 | McNeal | |
| 4,944,294 A | 7/1990 | Borek, Jr. | |
| 4,966,140 A | 10/1990 | Herzberg | |
| 5,020,533 A | 6/1991 | Hubbard et al. | |
| 5,067,174 A * | 11/1991 | Ritchey et al. | 2/10 |
| 5,099,525 A * | 3/1992 | Millauro | 2/9 |
| 5,107,547 A | 4/1992 | Scheu | |
| 5,113,528 A | 5/1992 | Burke, Jr. et al. | |
| 5,150,703 A | 9/1992 | Hubbard et al. | |
| 5,261,398 A * | 11/1993 | Sobolik | 128/206.23 |
| 5,303,423 A * | 4/1994 | Gazzara et al. | 2/9 |
| D355,714 S | 2/1995 | Hubbard et al. | |
| D355,715 S | 2/1995 | Hubbard et al. | |
| 5,406,944 A * | 4/1995 | Gazzara | 128/206.19 |

(Continued)

OTHER PUBLICATIONS

Education & Training, Managing Infection Control, Mar. 2004, p. 84.

(Continued)

*Primary Examiner*—Gary L. Welch
*Assistant Examiner*—Nathan E Durham
(74) *Attorney, Agent, or Firm*—Grady K. Bergen; Griggs Bergen LLP (57) ABSTRACT

A face and eye covering device includes a face cover configured for covering the nose and mouth of a wearer. The face cover is air permeable to allow the passage of air therethrough to facilitate breathing when worn over the wearer's nose or mouth. An eye shield is coupled to the face cover. The eye shield includes a lens and a lens protector releasably coupled to the lens. At least a portion of the lens and lens protector are transparent to allow visual perception therethrough.

15 Claims, 8 Drawing Sheets

U.S. PATENT DOCUMENTS

| | | | | |
|---|---|---|---|---|
| 5,446,925 A | * | 9/1995 | Baker et al. | 2/9 |
| 5,561,863 A | * | 10/1996 | Carlson, II | 2/206 |
| 5,584,078 A | * | 12/1996 | Saboory | 2/427 |
| 5,592,698 A | * | 1/1997 | Woods | 2/424 |
| 5,671,483 A | * | 9/1997 | Reuber | 2/424 |
| 5,682,879 A | * | 11/1997 | Bowers | 128/206.19 |
| 5,704,349 A | * | 1/1998 | Hubbard et al. | 128/206.19 |
| 5,740,560 A | * | 4/1998 | Muoio | 2/434 |
| 5,765,556 A | | 6/1998 | Brunson | |
| 5,813,398 A | * | 9/1998 | Baird et al. | 128/201.17 |
| 5,865,196 A | * | 2/1999 | Foote | 132/319 |
| 6,026,511 A | | 2/2000 | Baumann et al. | |
| 6,213,125 B1 | | 4/2001 | Reese et al. | |
| 6,216,695 B1 | * | 4/2001 | Ruben | 128/206.19 |
| 6,388,813 B1 | | 5/2002 | Wilson et al. | |
| 6,461,709 B1 | * | 10/2002 | Janssen et al. | 428/41.7 |
| 6,463,590 B1 | | 10/2002 | Dean et al. | |
| 6,536,045 B1 | | 3/2003 | Wilson et al. | |
| 6,568,392 B1 | * | 5/2003 | Bostock et al. | 128/206.19 |
| 6,694,971 B2 | | 2/2004 | Schroeder | |
| 6,984,037 B2 | * | 1/2006 | Bleau | 351/83 |
| 2003/0158025 A1 | * | 8/2003 | Lintala et al. | 493/357 |
| 2004/0172002 A1 | * | 9/2004 | Nelson et al. | 604/385.02 |

OTHER PUBLICATIONS

Infection Control Progress Report, Supplement to Outpatient Surgery Magazine, May 2004, pp. 38 and 40.

* cited by examiner

FACE AND EYE COVERING DEVICE

This application claims the benefit of U.S. Provisional Patent Application No. 60/479,652, filed Jun. 19, 2003.

BACKGROUND

The invention relates generally to protective coverings for the face and eyes.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
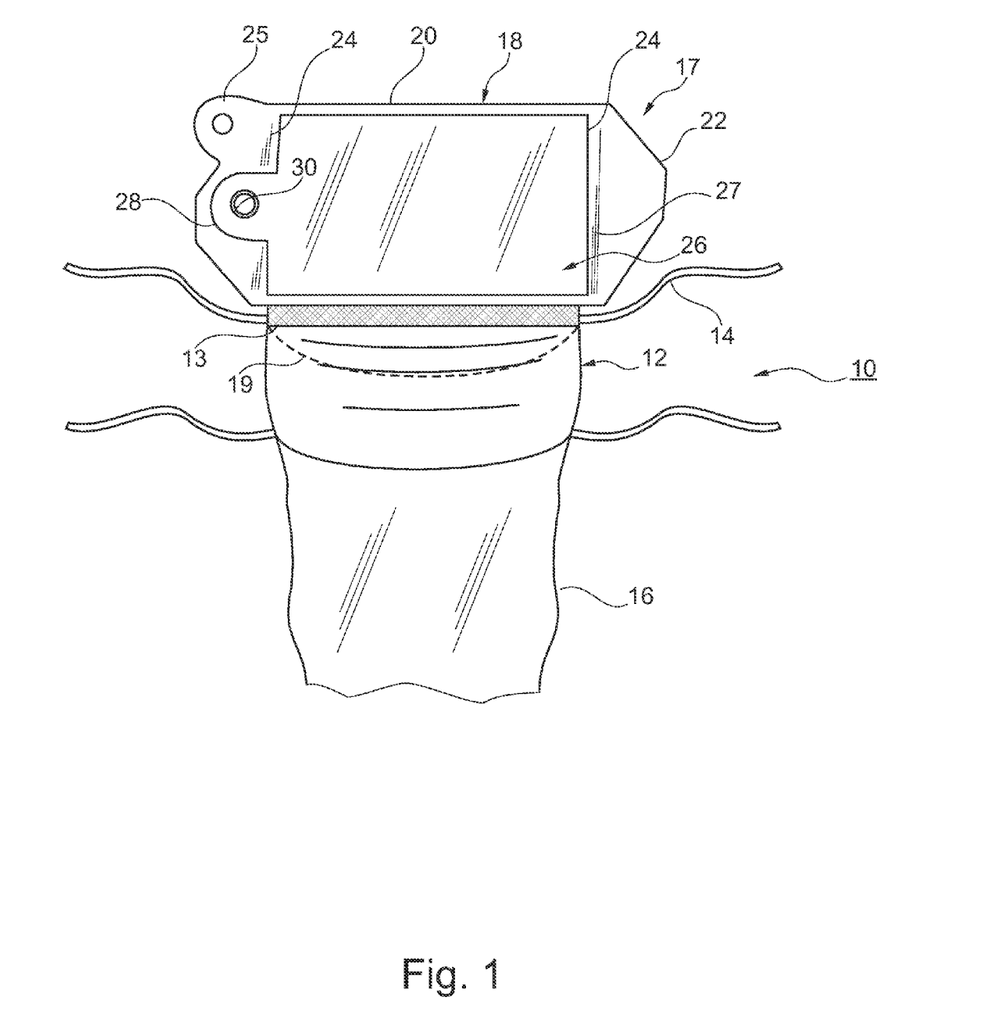
FIG. 1 is a front elevational view of a face and eye covering device, constructed in accordance with the invention.

Referring to FIG. 1, a protective face covering device 10 is shown. The device 10 includes a face mask 12 for covering the mouth and face. The face mask 12 may be configured for covering a portion of the wearer's cheeks and chin, as well. The face mask 12 may be the same or similar to those used in surgical or medical environments or in clean room or other sterile environments. Additionally, the face mask 12 may be that such as used in industrial or non-medical applications or environments for preventing the inhalation of dust, debris or other airborne particles.

The face mask 12 may be air permeable to facilitate breathing when worn over the wearer's nose or mouth. The face mask 12 may be formed from woven or non-woven fiber material that is air permeable to allow the passage of air therethrough. It may be in the form of a flexible fabric or paper material, which may be a single or multi-layer material. The mask 12 may also be formed with several overlapping or pleated layers of the flexible fabric or paper material. The face mask 12 may also be formed from a generally rigid material and formed into a suitable shape configured for covering the mouth and nose, such as a cup or cone shape. The mask 12 may constitute a filter or be provided with a filter portion (not shown) to prevent the passage of bacteria through the mask and to prevent or reduce fogging, as is described in U.S. Pat. No. 4,419,993, which is herein incorporated by reference. A darkened area or strip 13 may be provided on the mask 12 to reduce glare from overhead light.

Securing devices 14 may be coupled to the mask 12 for securing the device 10 to the face of the wearer. The securing devices 14 may be in the form of straps that are tied about the user's head. Alternatively, the devices may be elastic loops, straps or other members that loop over or secure to the wearer's ears or wrap about the wearer's head. Other securing devices that are known to those skilled in the art may also be used.

In the embodiment shown in FIG. 1, a neck flap 16 is coupled to the mask 12. The neck flap 16 may be formed from a flexible material that extends downward from the mask 12 when worn, and may be tucked into the wearer's shirt or clothing. In certain embodiments, the neck flap 16 may not be present or may be eliminated.

An eye shield 17 of the device 10 is coupled to the mask 12. The shield 17 includes a lens 18 that may be permanently or removably coupled to the mask 12. As shown in FIG. 1, the lens 18 may be coupled to the mask 12 along the lower edge of the lens 18. In the embodiment shown, a lower extending portion 19 extends downward and overlaps a portion of the mask 12. The lower portion 19 may be coupled to the material of the mask through various means, such as ultrasonic welding, thermal bonding, permanent and repositionable adhesives, stapling, riveting, stitching, hook and loop fasteners (eg. Velcro®), snaps, slots and pegs, etc.

The lens 18 may be a relatively thin sheet of liquid impervious material with all or a portion of the sheet being transparent. The lens may be of a polymeric material (eg. polyester, Mylar, etc.) and be relatively flexible, particular those of lower thickness, so that it may be easily bent, manipulated or otherwise flexed to facilitate creaseless wrapping or curving of the lens 18 around the wearer's head or face. The sheet may have a sufficient stiffness or rigidity, however, so that it stands upright without folding under its own weight and be of sufficient thickness so that it may serve as a protective barrier for shielding the eyes from flying particles or liquid spray or droplets. The lens 18 may be of varying thickness. A suitable range for the thickness of the lens 18 is from about 3 mils to 50 mils, more particularly from about 3 mils to about 10 mils, and still more particularly from about 4 mils to about 7 mils.

The lens 18 may be of a variety of configurations and may be configured to extend across both the wearer's eyes, as well as to either side the wearer's head and forehead. As shown in FIG. 1, the lens has a central eye shield portion 20 that extends across the eyes of the wearer. Opposite side portions 22 extend from either side of the eye shield portion 20. The lens 18 may be provided with creases or bends 24, as shown, so that side portions 22 wrap around either side of the wearer's head. In certain embodiments, a nose cutout (not shown), which may also be provided with or without a separate nose piece (not shown), may be provided to facilitate placing of the device 10 on the wearer's face. An example of such a mask and eye shield combination is described in U.S. Pat. No. 6,026,511, which is herein incorporated by reference.

The lens 18 may also be provided with loops or straps (not shown) or other attachment devices, in addition to those of the mask 12, to facilitate attachment of the shield 17 to the wearer's head. A grasping portion or tab 25 may be provided with the lens. The portion 25 may be formed from a continuous and projecting portion of the lens 18.

The lens 18 may be treated or coated with anti-fog and anti-glare coatings and also be tinted or shaded (eg. amber, smoke, etc.). Examples of commercially available material for the lens 18 are the 4 mil and 6.8 mil polyester films, available as 3M™ Anti-Fog Protective Optical Film from 3M Company.

Figure 2:
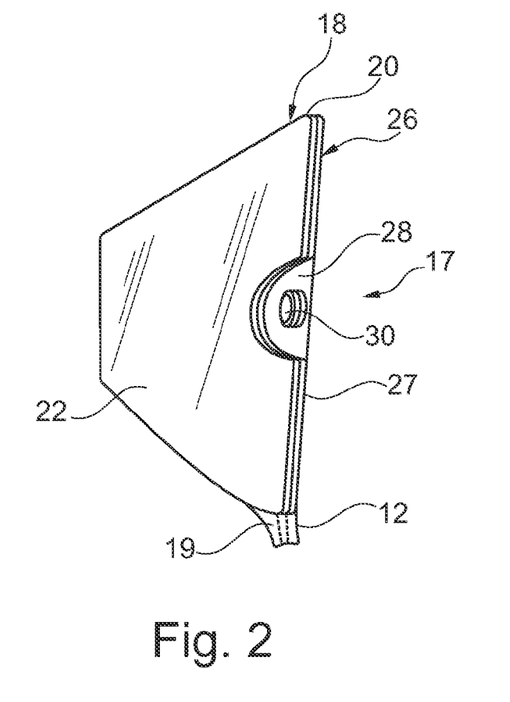
FIG. 2 is a side elevational view of an eye shield of the device of FIG. 1.

Releasably coupled to the lens 18 is a lens protector 26 of the eye shield 17. The lens protector 26 overlays all or a portion of the outer surface of the lens 18. In the embodiment shown, the lens protector 26 extends generally over the central eye portion 20 of the lens 18. All or a portion of the lens protector 26 may be transparent to allow visual perception therethrough. The lens protector 26 may be impervious to liquids and may be formed from an optically transparent polymeric material, such as polyester or polyethylene terephalate (PET). The lens protector 26 may be formed from one or more (eg. 2 to 6) lens protector film layers 27 (FIG. 2). The lens protector film layers 27 may have a thickness ranging from about 0.01 mils to about 3 mils, more particularly from about 0.05 mils to about 2 mils. The protector layers 27 may also be treated or coated with anti-fog and anti-glare coatings and also be tinted or shaded (eg. amber, smoke, etc.).

One or more pull tabs 28 may be provided with each protector layer 27. The pull tab 28 may be located along one or more side edges of the lens protector layers 27 and may be formed from a continuous and projecting portion of the material forming the layer 27. Alternatively, the pull tab 28 may be a separate element or member that is coupled to the lens protector layer 27. All or a portion of each pull tab 28 or a portion of each protective layer 27 may be colored with different colors (eg. red, yellow, green, etc.) or provided with different indicia (eg. numerical indicia 1, 2, 3, etc.) to facilitate distinguishing of the different layers 27.

Figure 3:
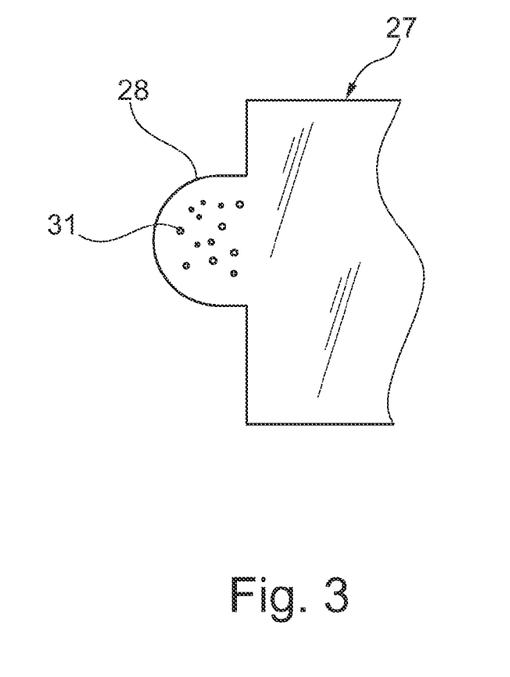
FIG. 3 is a front elevational view of a shield protector layer of the eye shield of FIG. 2, shown with a pull tab having a textured surface.

The pull tab 28 formed from a projecting portion of the layer 27 may be provided with a cutout portion, such as the aperture 30, configured to facilitate grasping of the tab 28. The aperture 30 may be sized for the insertion of one or more fingers. Alternatively, the pull tab 28 may be provided with a roughened or textured surface, such as the plurality of small dimples or protuberances 31 formed on the surface of the tab 28, as shown in FIG. 3. The grasping portion 25 of the lens 18 may also be provided with a similar cutout or textured surface to facilitate grasping of the lens 18.

Figure 4:
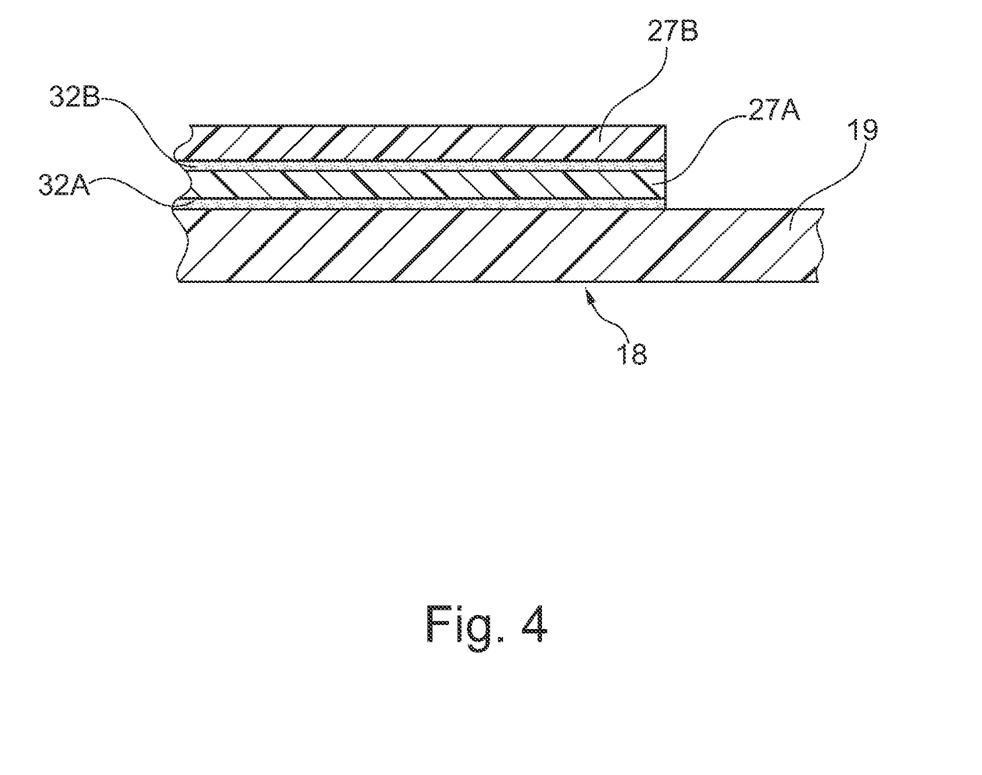
FIG. 4 is a cross-sectional view of a portion of the eye shield of FIG. 2.

The protective layers 27 may be releasably coupled to the lens 18 by means of a releasable adhesive. As shown in FIG. 4, adhesive layers 32A, 32B are used to secure protective layers 27A, 27B to the eye portion 20 of the lens 18. The adhesive 32A releasably couples the innermost layer 27A to the outer surface of the lens 18. Similarly, the adhesive layer 32B releasably couples the next adjacent outer layer 27B to the outer surface of the layer 27A. Additional layers lens protective layers can be releasably coupled in a similar manner.

The shield 17 may be preformed by laminating the lens and protective layers together in a continuous, uncut length that is then cut to the desired shape. As shown in FIG. 4, the laminated layers may be scored along a line and the protective layers 27A, 27B removed from the laminate to form the portion 19 of the lens 18. The layers of the laminate may also be temporarily separated or split, scored or cut to the desired shape to form the grasping portions 25, pull tabs 30, side portions 22, cutouts 30, etc., as are described herein, in a similar manner.

The adhesive 32 may be a low tack, pressure sensitive adhesive capable of holding the protective layers 27 in place upon the lens 18, while readily releasing from the lens 27 or underlying protective layer 27 during removal of the protective layer, as is described below. The adhesive may be a water or oil based adhesive. Acrylic adhesives are particularly suited for this application. The adhesive 32 may be optically clear when the protective layers 27 are laminated and applied to the lens 27 and may release cleanly without leaving any visible residue that would obscure vision. The adhesive 32 may be applied to the layers 27 as a uniform coating over generally the entire surface of the layer 27. Alternatively, the adhesive 32 may be applied to only portions of the layers 27, such as strips or sections along the periphery or interior sections of the layers. The adhesive may be applied as continuous or non-continuous sections or strips. The adhesive layer 32 may have only a nominal thickness or a thickness sufficient to perform the releasable coupling function, as described herein.

Alternatively, non-adhesive, releasable fasteners may be used to couple the protective layers 27 to the lens 18. This may include such things as snaps, hook and loop fasteners, hole and posts, etc.

In use, the device 10 is worn with the face mask portion 12 positioned over the mouth and nose in a conventional manner. The device 10 is secured to the wearer's head by means of the straps or securing elements 14. The neck flap 16 may be tucked into the shirt or clothing of the wearer to protect the wearer's neck. When the mask 12 is properly positioned, the eye shield 17 will extend across and cover the wearer's eyes.

As the device 10 is being worn, the eye shield 17 may become splattered with flying matter, such as blood, bone chips, water, paint, etc. This may obscure the wearer's vision through the shield 17. If so, the wearer or an assistant may remove the outermost protective layer 27 to clear the eye shield portion 20 of the shield 17. This may be done by grasping the pull tab 28 and peeling away the outermost layer 27. This effectively clears the splattered material from the lens 18. Because the lens 18 may be somewhat flexible, it may be beneficial to hold the lens 18 during removal of the protective layers 27. The user may grasp the lens 18 along the side portions 22 or the grasping portion 25, if such a grasping portion is provided. The pull tab 28 of the outermost protective layer 27 may then be grasped and the layer 27 may be removed from the shield 17. This removes any debris or splatters that may have covered the surface of the now removed protective layer 27 so that underlying eye shield portion 20 is cleared and the wearer's vision is no longer obscured. The layers 27 may be sequentially removed one at a time as needed to clear the shield portion 20.

Figure 5:
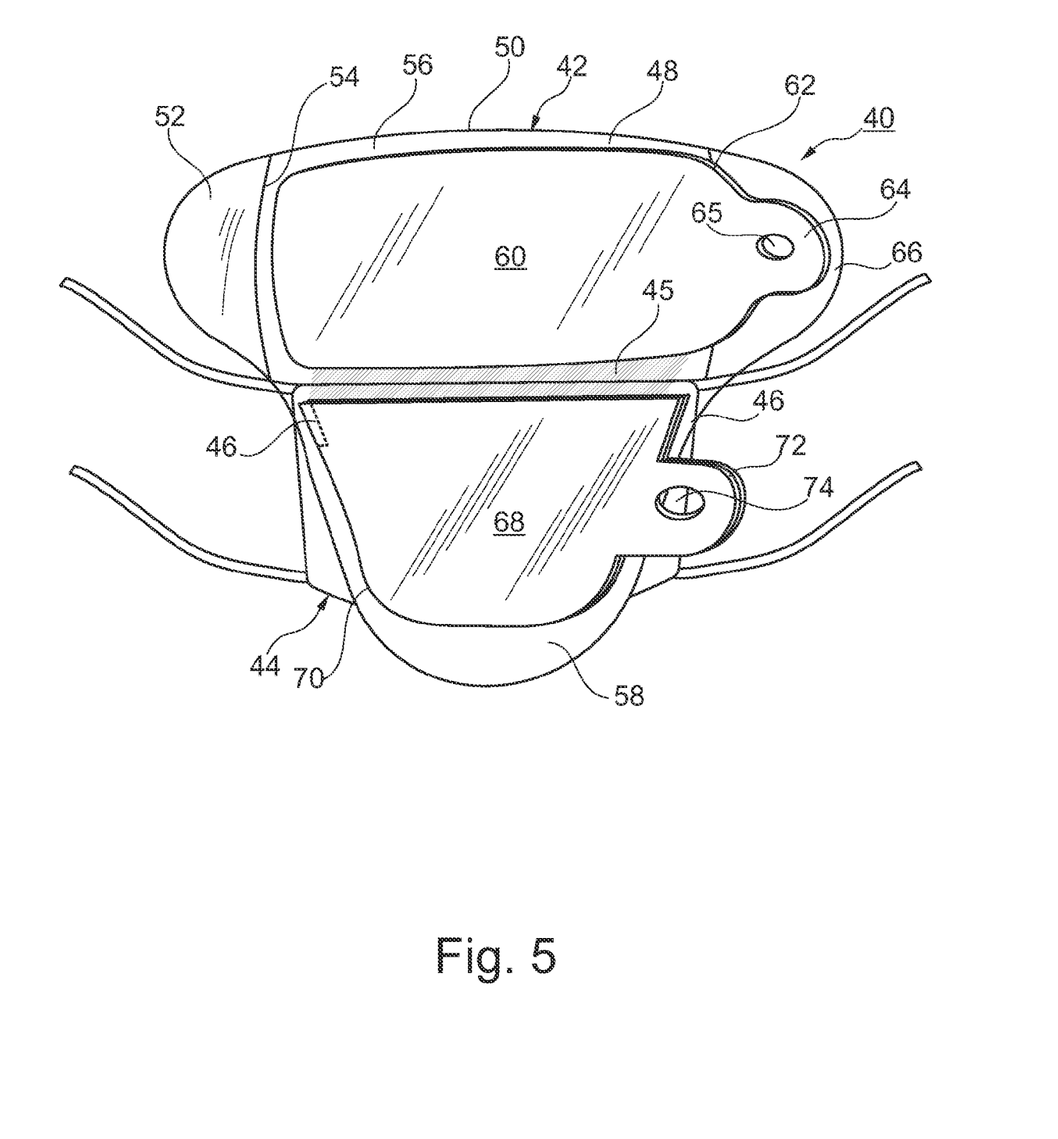
FIG. 5 is front elevational view of a another embodiment of a face and eye covering device, constructed in accordance with the invention.
Figure 6:
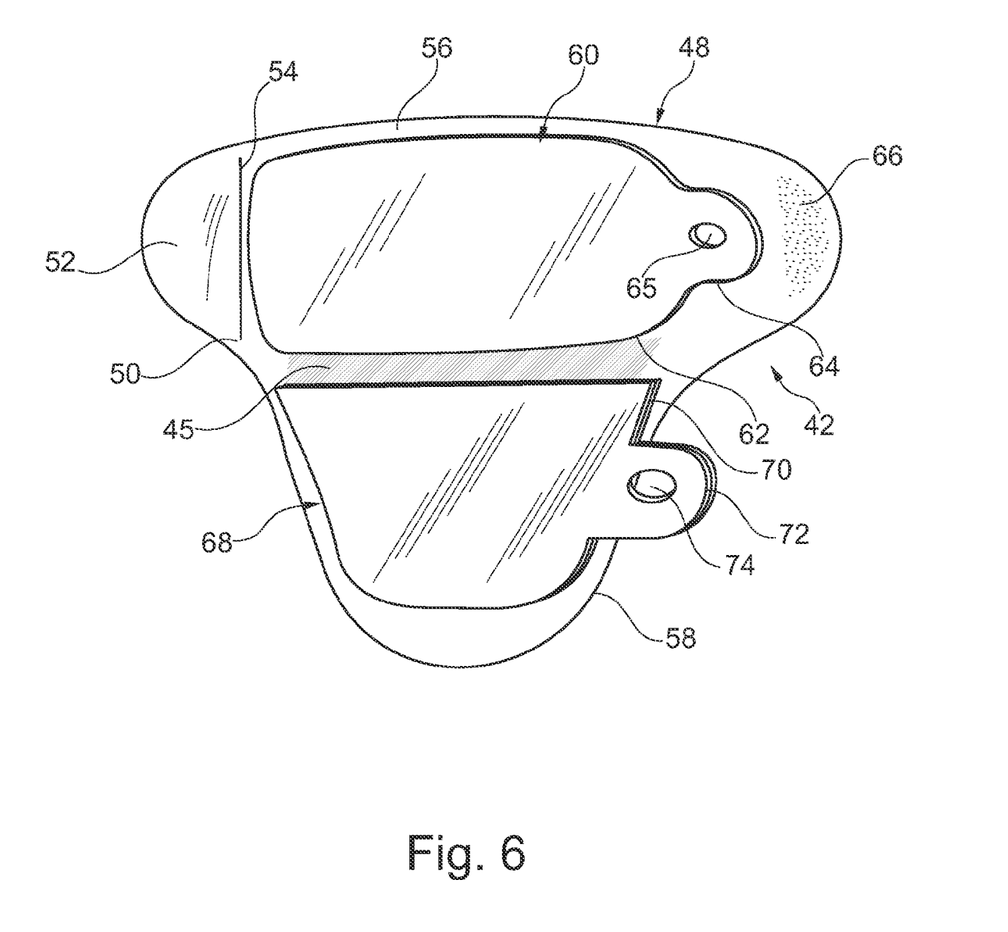
FIG. 6 is a front elevational view of an eye shield of the face and eye covering device of FIG. 5.

Referring to FIGS. 5 and 6, another embodiment of a face covering device 40 is shown. The device 40 includes a shield 42 coupled to a mask 44, as at sonic weld points 46. A darkened area or strip 45 may be provided on the shield 42 at a position generally corresponding to the bridge of the wearer's nose beneath the eyes to reduce glare from overhead light. In the embodiment shown, the shield 42 is coupled on the outward side of the mask 44. The mask 44 may be similar to the mask 12. A neck flap (not shown) may optionally be included.

FIG. 6 shows the shield 42 removed from the mask 44. The shield 42 includes a lens or shield substrate 48. The substrate 48 includes an upper portion 50 that is configured to generally cover the wearer's eyes. At least a portion of the upper portion 50 that covers the wearer's eyes is optically transparent to allow visual perception therethrough. The upper portion 50 may be similar in configuration to the lens 18 of the device 10 and may include side portions 52 and creases or bends 54 that define a central eye shield portion 56.

The substrate 48 includes lower face mask portion 58 that extends downward from the upper portion 50 and is generally configured to extend over and cover the mask 44 or lower portion of the wearer's face when the device 40 is worn.

Releasably coupled to the central portion 56 of the substrate 48 is an upper shield protector 60. The shield protector 60 may be similar to the shield protector 24 of the device 10 and include one or more shield protector layers 62 releasably coupled to the substrate 48 or an adjacent layer 62. A grasping portion or pull tab 64, which may have a cutout 65 or textured surface, may also be provided. A grasping portion or the side portion 52 may also be provided with a cutout or textured surface, such as the surface 66 to facilitate removal of the layers from the upper portion 50 of the substrate 48.

All or a portion of the lower face mask portion 58 of the substrate 48 may be provided with a lower shield protector 68, which is separate from the shield protector 60. Alternatively, a single shield protector may be employed that covers both the upper portion 50 and lower portion 58 of the substrate 48. The lower shield protector 68 may be formed from one or more shield protector layers 70 releasably coupled to the lower portion 58 of the substrate 48 or an adjacent layer 70. A grasping portion or pull tab 72, which may have a cutout 74 or textured surface, may also be provided. Since the lower portion 58 and shield protector 68 do not cover the eyes, these areas may lack optical transparency, if desired.

In use, the device 40 is positioned on the wearer's face. As splatters or other debris accumulate on the surface of either of the shield protectors 60, 68, the protective layers 62, 70 may be sequentially removed one at a time to clear the shield portions 56 and 58, respectively.

Figure 7:
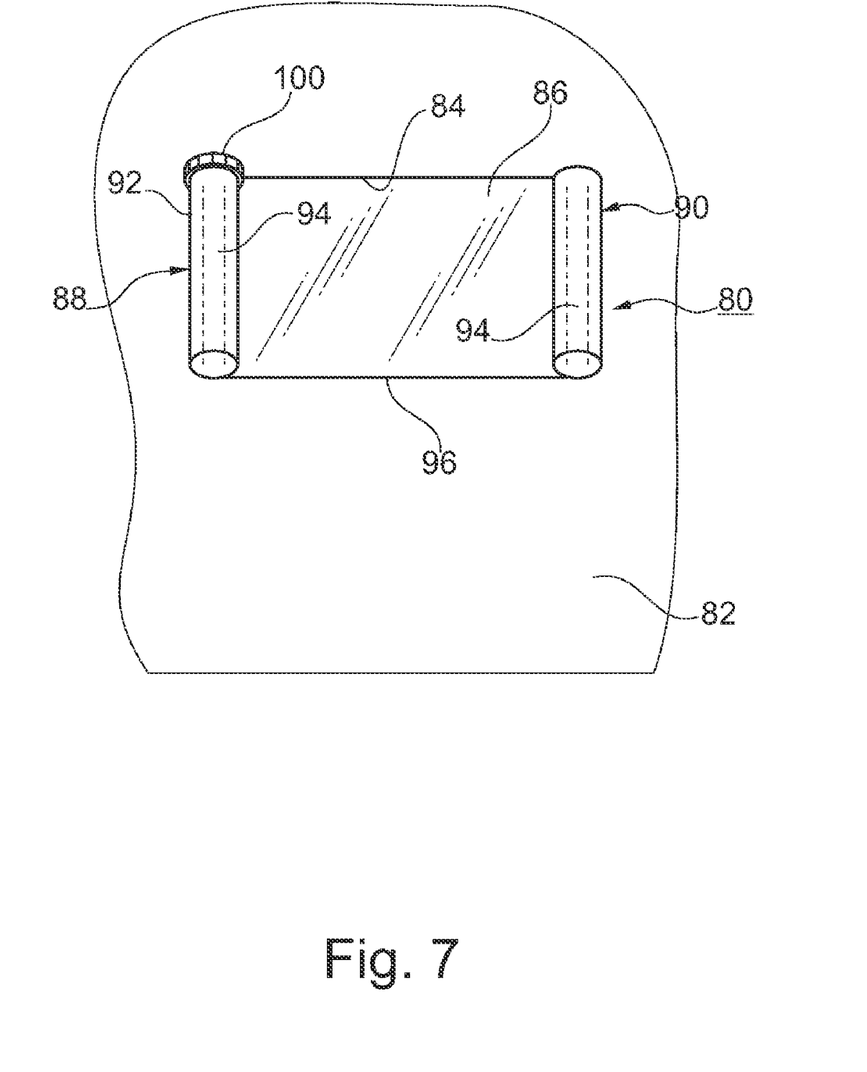
FIG. 7 is a front elevational view of still another embodiment of a face and eye covering device, constructed in accordance with the invention.

Referring to FIG. 7, another embodiment of a face and eye covering device 80 is shown. The device 80 includes a hood 82 that may be formed of a woven or non-woven fiber material, such as flexible cloth or paper material. The hood 82 may also be formed of other materials, which may or may not be permeable to air. The hood 82 fits over the wearer's head and neck and constitutes a face cover. An opening 84 is formed in the hood and a face shield 86 is coupled to the hood 82 and positioned within the opening to thereby close off the opening 84. The shield 86 may be of varying thickness and formed from the same or similar materials as the shield and lenses previously described. All or a portion of the shield 86 may be optically transparent. The shield 86 may be flexible but have some degree of stiffness or rigidity to prevent it from collapsing, bending or folding during normal use of the device 80.

Coupled to the hood 82 and positioned at either side of the opening 84 are opposite reel assemblies 88, 90. Each reel assembly 88, 90 may include a housing 92 that may be permanently or removably coupled to the hood 82 by various means such as ultrasonic welding, thermal bonding, permanent and repositionable adhesives or glues, stapling, riveting, stitching, hook and loop fasteners (eg. Velcro®), snaps, slots and pegs, etc.

Figure 8:
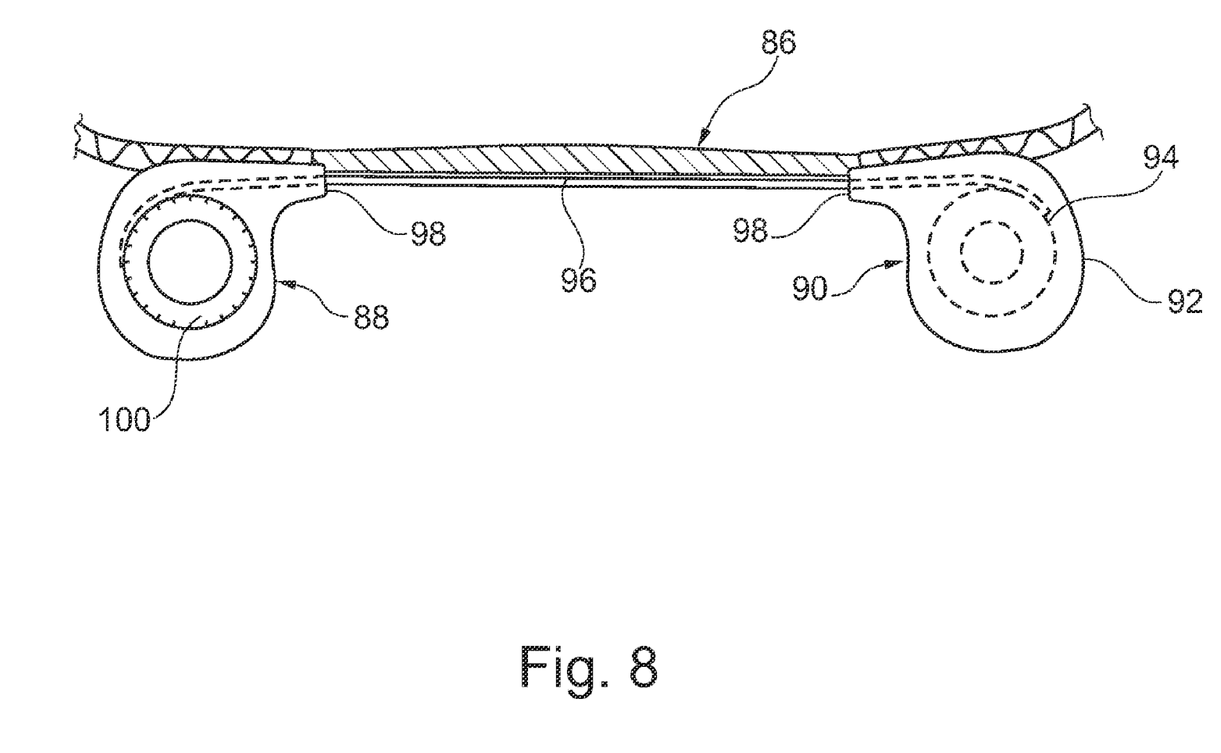
FIG. 8 is a plan view of a protective film reel assembly for a shield of the device of FIG. 7.

A film reel 94 for storing a continuous length of protective film 96 is housed within each housing 92. The film reels 94 are rotatably coupled to the housing 92 of each reel assembly 88, 90. As shown, the reel assembly 90 is a film feed assembly with a length of unused film being stored on the reel 94 of assembly 90. The film 96 may be the same or similar to the material forming the protective layers 27, previously described, and may be optically transparent to allow visual perception therethrough. The film 96 passes through openings 98 formed in each of the housings 92 of the assemblies 88, 90 and is oriented so that it extends across and covers all or a portion of the shield 86.

The reel assembly 88 is provided with a dial 100 or other advancement mechanism for advancing the film 96 onto the reel 94 of assembly 88. A similar advancement mechanism (not shown) may be provided on reel assembly 90, if desired. One type of advancement mechanism that may be used is that described in U.S. Pat. No. 4,428,081, which is herein incorporated by reference.

In use, the device 80 is positioned on the wearer's head so that the shield 86 is positioned generally over the wearer's face, with the hood 82 covering the wearer's head and neck. Initially, a clean area of the film 96 is positioned over the shield 86. As the film 96 becomes splattered or covered with debris so that the wearer's vision is obscured, the film may be advanced using the advancement mechanism 100 so that the reel 94 of assembly 88 takes up and stores the soiled film within the housing 92. A fresh or clean length of film is simultaneously advanced from assembly 90 and over the shield 86. This is repeated as necessary.

In an alternate embodiment of the device 100, the reel assembly may be eliminated and one or more individual protective sheets or layers, which may include a grasping portion or pull tab, may be releasably coupled to the shield 86 and removed in a similar manner as described with respect to the embodiments of FIGS. 1-6.

Figure 9:
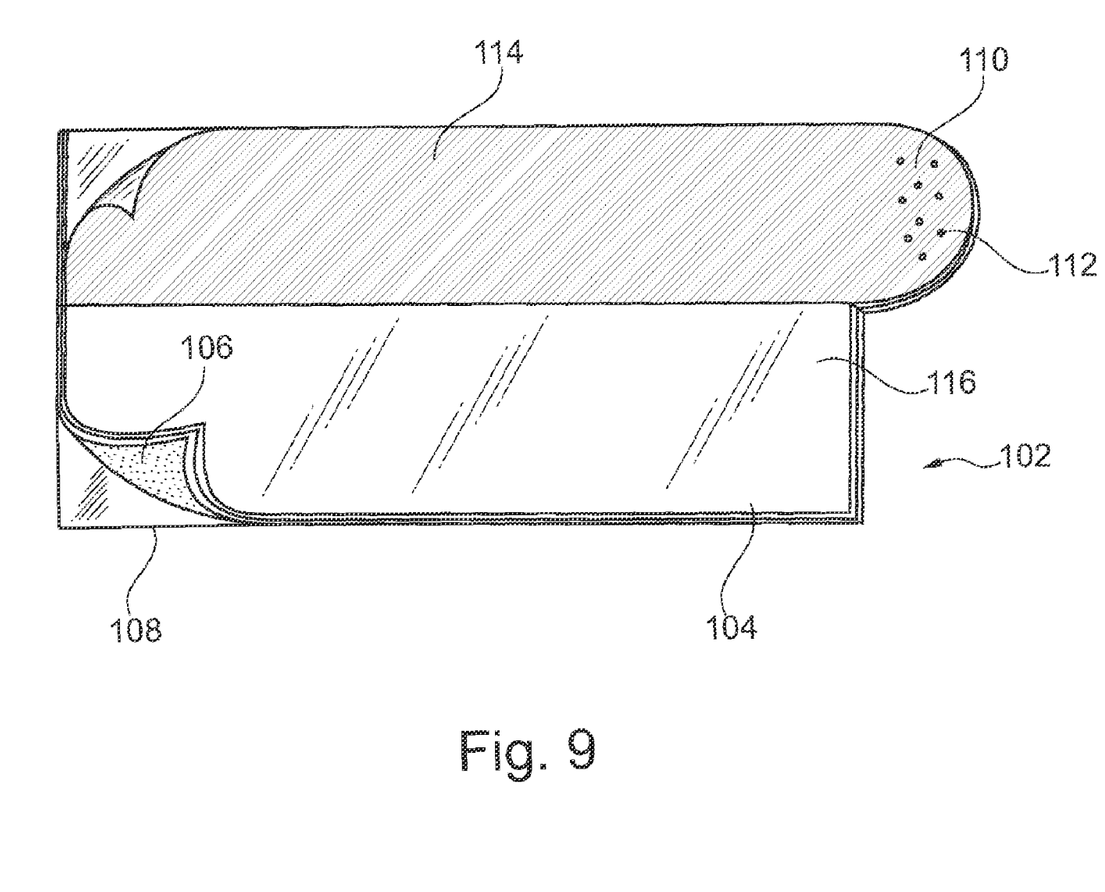
FIG. 9 is a top perspective view of a partially tinted shield protector assembly, shown with a corner of a release liner of the shield protector assembly and an upper tinted film layer partially peeled away.

Referring to FIG. 9, a partially tinted shield protector assembly 102 that may be applied to an existing mask and shield combination of the type having a lens or transparent shield coupled to a mask, such as those previously described, is shown. The assembly 102 includes one or more shield protector film layers 104, each having a layer of releasable, pressure sensitive adhesive 106 applied to one side that may releasably couple adjacent layers 104 to one another. In the embodiment shown, the film layers 104 with the applied adhesive are optically clear. The film layers 104 and adhesive 106 may be the same or similar to that of the previously discussed embodiments. A removable release liner 108 may be applied to the adhesive of the bottom or lower layer to protect the adhesive of the bottom film layer 104.

Each film layer 104 may have a projecting grasping portion or pull tab 110 having a textured surface 112.

In the embodiment shown, the uppermost film layer 104 is partially tinted (smoke, amber, etc.) generally across the width of the upper half 114 of the film layer. The lower half 116 of the uppermost film layer 104 may be non-tinted.

In use, the shield protector assembly 102 may be applied to the lens of a preexisting mask and shield combination. The protector assembly 102 may be configured and sized so that it may be applied to most existing mask and shield combinations. If necessary, the assembly 102 may also be cut to size or shape by the user using a scissors, razor or other commonly used cutting tool for fitting on any existing shields. The appropriately sized assembly 102 with the liner 108 removed may then be applied to the outer surface of the lens of the mask and shield. This is done by removing the release liner 108 of the bottom layer 104 to expose the adhesive 106 thereon. The layers 104 are then positioned on the lens of the mask and shield, with the adhesive layer 106 on the bottom layer 104 releasably coupling the assembly 102 to the outer surface of the lens.

The assembly 102 has particular application for use in laser surgery operations or applications where there is a need for initially providing eye protection from bright light. Thus, during such operations, the wearer may look through the upper tinted portion to protect the wearer's eyes from laser or other bright light. The wearer may also look through the non-tinted lower portion 116, tilting or adjusting the orientation of their head if necessary, to see more clearly without the tinting. Upon completion of the activity where protection from bright light is necessary, the wearer or an assistant may remove the uppermost tinted layer 104 by pulling the pull tab 110 and peeling away the uppermost layer 104 to expose the remaining layers 104 or lens of the mask. The underlying layers 104 or lens of the mask and shield combination may be a non-tinted. If desired, however, the underlying layers 104 may be similarly tinted as well. It should be apparent to those skilled in the art that the partially tinted construction of the assembly 102, as described, could also be employed on the previously described embodiments as well.

The covering devices described herein and components thereof may be disposable and manufactured for a single use or they may be reusable. In certain instances the shield portion may be manufactured and supplied separately from the mask or hood with which it is to be used. The devices may be sterile or sterilizable. Sterilization may be done through sterilization techniques that are well known in the art, such as chemical, radiation or heat sterilization methods. The devices may be packaged in a manner to maintain the sterile integrity of the device until they are needed.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A method of forming a face and eye covering device comprising:

laminating at least two layers of flexible material together and then cutting the laminated layers into a desired shape to form an eye shield, the at least two layers of flexible material comprising a lens and at least one lens protector film layer wherein the lens has a greater thickness than any single lens protector film layer, and wherein at least a portion of the at least two layers is transparent to allow visual perception through the at least two layers forming the eye shield, and wherein the at least two laminated layers are releasable so that one of the layers may be selectively removed from the other; and directly coupling the eye shield to a face cover along a lower portion of the lens wherein the face cover is configured for covering the nose and mouth of a wearer, the face cover being air permeable to allow the passage of air therethrough to facilitate breathing when worn over the wearer's nose or mouth.

2. The method of claim 1, wherein:
the at least two layers of flexible material are laminated together with a uniform coating of an optically clear adhesive.

3. The method of claim 2, wherein:
the adhesive covers generally the entire surface of the layers.

4. The method of claim 1, wherein:
the at least one lens protector film layer of the at least two layers forming the eye shield has a grasping portion that is provided to facilitate removal of said at least one lens protector film layer of the at least two layers.

5. The meted of claim 4, wherein:
the grasping portion is provided with at least one of a textured surface or cutout to facilitate grasping and removing of said at least one lens protector film layer of the at least two layers.

6. The method of claim 1, wherein:
there are at least three layers of flexible material laminated together that are then cut into the desired shape to form the eye shield wherein the at least three layers of flexible material comprises the lens and at least two lens protector film layers.

7. The method of claim 6, wherein:
the at least two lens protector film layers of the at least three layers has a projecting grasping portion that is provided to facilitate removal of said at least two lens protector film layers of the at least three layers, and wherein the grasping portion is provided with indicia to facilitate distinguishing each of the layers.

8. The method of claim 1, wherein:
all or a portion of at least one of the layers of flexible material is tinted or shaded.

9. The method of claim 1, further comprising:
providing a securing device for the eye shield for securing the eye shield to the head of a wearer.

10. The method of claim 1, wherein:
the lens of the at least two layers of flexible material has a thickness of from about 3 mils to about 50 mils, and the at least one lens protector film layer of the at least two layers of flexible material has a thickness of from about 0.01 to about 3 mils.

11. The method of claim 1, wherein:
the eye shield is sterilized or formed from sterile materials for use in a sterile environment.

12. The method of claim 1, wherein:
the eye shield is disposable.

13. The method of claim 1, wherein:
the eye shield has sufficient flexibility so that the eye shield is contourable.

14. The method of claim 1, wherein:
the eye shield is directly coupled to the face cover by at least one of ultrasonic welding, thermal bonding, permanent adhesives, repositionable adhesives, stapling, riveting, stitching, hook and loop fasteners, snap fasteners, slots and pegs.

15. The method of claim 1, wherein:
a portion of the eye shield extends over the face cover.

* * * * *